US008614315B2

(12) United States Patent
Bilgic

(10) Patent No.: US 8,614,315 B2
(45) Date of Patent: Dec. 24, 2013

(54) CEFDINIR AND CEFIXIME FORMULATIONS AND USES THEREOF

(76) Inventor: Mahmut Bilgic, Istanbul (TR)

(*) Notice: Subject to any disclaimer, the term of this patent is extended or adjusted under 35 U.S.C. 154(b) by 0 days.

(21) Appl. No.: 13/532,120

(22) Filed: Jun. 25, 2012

(65) Prior Publication Data

US 2013/0017156 A1 Jan. 17, 2013

Related U.S. Application Data

(63) Continuation-in-part of application No. PCT/TR2010/000239, filed on Dec. 3, 2010, and a continuation-in-part of application No. PCT/TR2010/000240, filed on Dec. 3, 2010, and a continuation-in-part of application No. PCT/TR2010/000241, filed on Dec. 3, 2010, and a continuation-in-part of application No. PCT/TR2010/000242, filed on Dec. 3, 2010, and a continuation-in-part of application No. PCT/TR2010/000257, filed on Dec. 24, 2010, and a continuation-in-part of application No. PCT/TR2010/000258, filed on Dec. 24, 2010, and a continuation-in-part of application No. PCT/TR2010/000259, filed on Dec. 24, 2010, and a continuation-in-part of application No. PCT/TR2010/000260, filed on Dec. 24, 2010, and a continuation-in-part of application No. PCT/TR2010/000261, filed on Dec. 24, 2010, and a continuation-in-part of application No. PCT/TR2010/000262, filed on Dec. 24, 2010.

(51) Int. Cl.
*C07D 501/00* (2006.01)

(52) U.S. Cl.
USPC .......................................................... 540/222

(58) Field of Classification Search
USPC ........................................................... 540/215
See application file for complete search history.

(56) References Cited

U.S. PATENT DOCUMENTS

| 2002/0051816 A1 | 5/2002 | Yamaguchi |
| 2005/0113355 A1 | 5/2005 | Duerst et al. |
| 2005/0131079 A1 | 6/2005 | Pujara |
| 2007/0128268 A1 | 6/2007 | Jennewein |
| 2007/0134325 A1 | 6/2007 | Yamaguchi |
| 2007/0191331 A1 | 8/2007 | Kansal et al. |
| 2007/0208173 A1 | 9/2007 | Kelly et al. |
| 2008/0103124 A1 | 5/2008 | Yoshioka et al. |
| 2008/0145879 A1 | 6/2008 | Orenga et al. |
| 2010/0035856 A1 | 2/2010 | Mertin et al. |

FOREIGN PATENT DOCUMENTS

| CN | 1706389 A | 12/2005 |
| CN | 1850087 A | 10/2006 |
| CN | 101352424 A | 1/2009 |
| CN | 101606913 A | 12/2009 |
| CN | 101744827 A | 6/2010 |
| DE | 102007002924 A1 | 7/2008 |
| EP | 2062581 A1 | 5/2009 |
| WO | WO-9709042 A1 | 3/1997 |
| WO | WO-9845299 A1 | 10/1998 |
| WO | WO-2004104010 A1 | 12/2004 |
| WO | WO 2006/008160 A1 * | 1/2006 |
| WO | WO 2006/035291 A1 * | 4/2006 |
| WO | WO-2006035291 A1 | 4/2006 |
| WO | WO 2006/053625 A1 * | 5/2006 |
| WO | WO-2006053625 A1 | 5/2006 |
| WO | WO-2006106529 A1 | 10/2006 |
| WO | WO-2007086012 A1 | 8/2007 |
| WO | WO-2007129176 A2 | 11/2007 |

OTHER PUBLICATIONS

Wermuth, Camille G. The Practice of Medicinal Chemistry, San Diego: Academic Press, 1996 pp. 203-237.*
Livermore et al., "Orthodox and unorthodox clavulanate combinations against extended-spectrum β-lactamase producers," *Clin Microbiol Infect.* 14(Suppl. 1):189-193 (2008).
Rawat et al., "In vitro evaluation of a new cefixime-clavulanic acid combination for gram-negative bacteria," *Southeast Asian J Trop Med Public Health* 40(1):131-139 (2009).
International Search Report for International Application No. PCT/TR2010/000239, mailed Feb. 24, 2011 (3 pages).
International Search Report for International Application No. PCT/TR2010/000240, mailed May 26, 2011 (7 pages).
Prakash et al., "Oral and parenteral therapeutic options for outpatient urinary infections caused by Enterobacteriaceae producing CTX-M extended-spectrum β-Lactamases," *Antimicrob Agents Chemother.* 53(3):1278-1280 (2009).
International Search Report for International Application No. PCT/TR2010/000241, mailed Feb. 18, 2011 (2 pages).
International Search Report for International Application No. PCT/TR2010/000242, mailed Mar. 9, 2011 (4 pages).
International Search Report for International Application No. PCT/TR2010/000257, mailed Mar. 29, 2011 (4 pages).
International Search Report for International Application No. PCT/TR2010/000258, mailed Mar. 29, 2011 (4 pages).
International Search Report for International Application No. PCT/TR2010/000259, mailed Mar. 29, 2011 (4 pages).
International Search Report for International Application No. PCT/TR2010/000260, mailed Mar. 29, 2011 (4 pages).
International Search Report for International Application No. PCT/TR2010/000261, mailed Mar. 24, 2011 (4 pages).
International Search Report for International Application No. PCT/TR2010/000262, mailed May 24, 2011 (4 pages).
Maskell et al., "Cephalosporin-resistance in the *Bacteroides fragilis* group and the effect of clavulanic acid," *J Antimicrob Chemother.* 13(1):23-30 (1984).
Search Report for Turkish Application No. 2009/09784, mailed Feb. 16, 2011 (7 pages).
Martin et al., "Increase in the activity of third-generation cephalosporins in combination with clavulanic acid and Sulbactam against *Bacteroides fragilis,*" *Med Lab Sci.* 47(3):163-167 (1990).

* cited by examiner

*Primary Examiner* — Noble Jarrell
*Assistant Examiner* — Laura Daniel
(74) *Attorney, Agent, or Firm* — Clark & Elbing, LLP

(57) ABSTRACT

The invention features pharmaceutically acceptable salts of cefdinir, including primary, secondary, and tertiary amine salts of cefdinir, and preparation methods, and pharmaceutical compositions including cefdinir. The invention also features water dispersible pharmaceutical dosage forms including cefdinir as active agent and methods for preparing the dosages. The invention also features tablet forms of cefixime characterized in that the tablets are in effervescent form. The invention also features the process for preparing effervescent tablet forms with cefdinir as active agents and pharmaceutical formulations obtained by the process.

10 Claims, No Drawings

CEFDINIR AND CEFIXIME FORMULATIONS AND USES THEREOF

CROSS-REFERENCE TO RELATED APPLICATIONS

This application is a continuation-in-part of PCT/TR2010/000239, PCT/TR2010/00240, PCT/TR2010/000241, and PCT/TR2010/000242, filed Dec. 3, 2010, and PCT/TR2010/000257, PCT/TR2010/000258, PCT/TR2010/000259, PCT/TR2010/000260, PCT/TR2010/000261, and PCT/TR2010/000262, filed Dec. 24, 2010, which are incorporated herein by reference in their entireties. This application is entitled to and claims priority benefits to application Ser. Nos. TR2009/09784, TR2009/09785, TR2009/09786, and TR2009/09787, filed Dec. 25, 2009, and TR2010/03547, filed May 4, 2010, and TR2010/03854, filed May 14, 2010.

BACKGROUND OF THE INVENTION

Cefdinir molecule which is shown with Formula I was first disclosed in the patent numbered BE897864 and its chemical name is (6R,7R)-7-[[(2Z)-(2-amino-4-thiazolyl)(hydroxyimino)acetyl]amino]-3-ethenyl-8-oxo-5-thia-1-azabicyclo[4.2.0]oct-2-en-2-carboxylic acid. This molecule, which is a third generation cephalosporin, is indicated for the treatment of several illnesses caused by gram positive and gram negative bacteria.

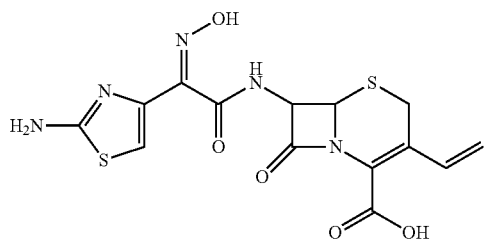

Formula I

Although in vitro tests prove that cefdinir is a highly potent antibiotic, the bioavailability of the finished product is less than expected and manufacturers experience problems while developing formulations due to its poor solubility in water, methanol, ethanol, acetone and many other organic solvents.

The product sold in the market under the tradename OMNICEF® is present in capsule and suspension forms. Clinic studies show that the bioavailability of the suspension product is 120% more than the bioavailability of the product in capsule form.

Although the suspension forms have higher bioavailability, use of this dosage form, especially for pediatric and geriatric patients, brings about the possibility of taking high and/or uncontrolled dose. Additionally, the fact that the suspensions have physical and chemical stability problems, they have short shelf life and high production costs, and the fact that they cause problems while transporting and use are disadvantageous for the manufacturers.

The difficulties encountered during the preparation of the formulation causes the problems in the physical properties of the final product, for instance the hardness and dispersion time parameters, or dose uniformity. This leads to some disadvantages for use of the patient and results in some problems about the bioavailability data since final product does not have dose uniformity.

The production processes in which the components are blended by dry granulation and/or blending method are preferred in order to prevent the problems resulting from solubility of cefdinir in the process. However, it is observed that pharmaceutical composition prepared by said process fails to satisfy the desired tablet hardness when the formulation prepared is compressed in a tablet form.

One of the problems frequently confronted in developing the formulations is that in the processes including wet granulation method once the active agent contacts with water, it is agglomerated due to its hydrophobic character and due to this reason, dose uniformity of the final product can not be provided.

Due to the reasons stated above it is necessary to provide new dosage forms in antibiotic theraphy in order to provide effective dosing, meet patient requirements, and to offer different alternatives to patients having special conditions, such as pediatric and geriatric patients. Furthermore, new processes for use in the preparation of formulations of effervescent compositions comprising cefdinir, where the composition is stable, has long shelf life, and high bio-availability, are also needed.

Cefixime was first described in European patent no EP0030630 (B1) and it is known with the chemical name of (6R,7R)-7-{[2-(2-amino-1,3-thiazol-4-yl)-2-(carboxymethyloxyimino)acetyl] amino}-3-ethenyl-8-oxo-5-thia-1-azabicyclo[4.2.0]oct-2-en-2-carboxylic acid (Formula V). It is defined as a third generation cephalosporin and indicated for use in the treatment of infections caused by gram positive and gram negative bacteria.

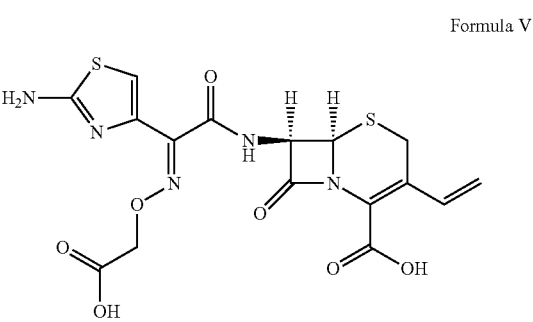 [SMILES: C=CC1=C(C(=O)O)N2C(=O)[C@@H](NC(=O)/C(=N/OCC(=O)O)c3csc(N)n3)[C@H]2SC1]

Formula V

Cefixime physically appears as white or light yellow crystal powder. It is freely soluble is methanol and propylene glycol, partially soluble in ethanol and acetone however it does not dissolve in ether, ethyl acetate, hexane and water. Its solubility in aqueous solutions changes with respect to the pH of the solution. Accordingly its solubility in a solution with a pH value of 3.2 is 0.5 mg/mL at room temperature; however when the pH of the solution is increased to 4.2 solubility increases to 18 mg/mL.

The product named as SUPRAX that is sold by Fujisawa/Astellas comprises cefixime as active agent and is present in oral tablet or oral suspension forms and in dosages comprising high amounts like 200 mg and 400 mg cefixime. Tablets comprising 200 mg or 400 mg active agents become very big in size when formulated with excipients and this causes problems about use of these tablets for patients having difficulty in swallowing, especially for pediatric and geriatric patients.

Suspension forms that are developed to overcome these problems are undesirable since it is possible to take uncontrolled or high dose and in addition to that they have chemical and physical stability problems, have high manufacturing cost, and cause problems when used or when carried.

In general although bioavailability values of suspension forms are better compared to the solid dosage forms, the fact that they have a short shelf life like 14 days makes them disadvantageous especially for the patients.

As seen from the above information it is necessary to form new dosage forms in order to provide effective dosing, to meet patient requirements, to provide different alternatives to patients with special requirements such as pediatric and geriatric patients and to provide new dosage forms for use in antibiotic treatment.

SUMMARY OF THE INVENTION

This application features the inventions disclosed in PCT/TR2010/000239, PCT/TR2010/00240, PCT/TR2010/000241, and PCT/TR2010/000242, filed Dec. 3, 2010, and PCT/TR2010/000257, PCT/TR2010/000258, PCT/TR2010/000259, PCT/TR2010/000260, PCT/TR2010/000261, and PCT/TR2010/000262, filed Dec. 24, 2010, the claims of which are hereby incorporated by reference in their entireties.

DETAILED DESCRIPTION OF THE INVENTION

Novel Cefdinir Salts

The present invention relates to organic amine salts of cefdinir, wherein said organic amines comprise at least one hydroxy group and relates to pharmaceutical dosage forms comprising said cefdinir salts.

The patent numbered EP1812449 discloses ammonium salt of cefdinir which can be used for the preparation cefdinir monohydrate. Another patent EP1546155, discloses ammonium and organic amine salts of cefdinir and use of these molecules as intermediates for synthesis of cefdinir.

As seen from these examples, prior art examples generally deal with the methods related to synthesis of cefdinir instead of its solubility problem.

Accordingly, present invention relates to the salts shown with the general Formula II.

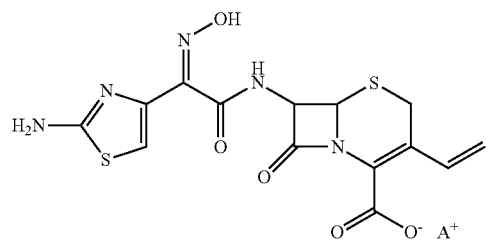

Formula II

The group shown with "A" in Formula II is a C1-C15 primary, secondary and/or tertiary amine characterized by containing at least one hydroxy group. Said amine can be selected from but not limited with a group comprising; ethanolamine, isopropanolamine, 1-deoxy-1-methylamino-sorbitol, 1-deoxy-1methylamino-D-glucitol, tris(hydroxymethyl)aminomethane, N-(tri(hydroxymethyl)methyl)glycine, N,N-Bis(2-hydroxyethylglycine), 2-methyl aminophenol, (2S,4R)-4-Hydroxy proline, thiamine.

In another aspect, one of the preferred molecules according to the present invention is the cefdinir salt shown with Formula III.

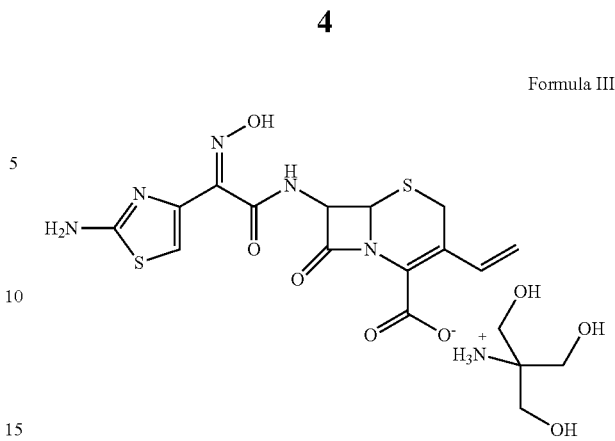

Formula III

In another aspect, one of the preferred molecules according to the present invention is the cefdinir salt shown with Formula IV.

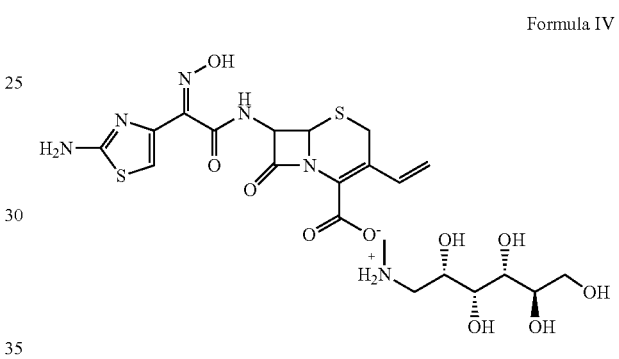

Formula IV

Inventors have found that cefdinir salts of the present invention have better water solubility compared to cefdinir in free base form and amine salts of cefdinir that do not comprise a hydroxy group which are known from the prior art.

In general, salts shown with Formula II are obtained with conventional techniques known from the prior art.

In another aspect, the present invention relates to use of the amine salts of cefdinir according to the present invention in solid and liquid dosage forms.

In another aspect, the present invention relates to use of the amine salts of cefdinir according to the present invention in dosage forms suitable for oral, buccal, sublingual application.

In another aspect, the present invention relates to use of the amine salts of cefdinir according to the present invention in pharmaceutical formulations in the form of film tablets, extended release tablets, modified release tablets, chewable tablets, effervescent tablets, effervescent granules, water dispersible tablet, water dispersible granules.

Amine salts of the present invention that are used in said pharmaceutical compositions can be in amorphous or crystal form.

In another aspect, the present invention relates to use of amine salts of cefdinir according to present invention in amounts equivalent to 1-4000 mg cefdinir.

In another aspect, the present invention relates to use of amine salts of cefdinir according to present invention and pharmaceutical compositions comprising them for the treatment of infections caused by gram positive and gram negative bacteria.

Molecules according to the present invention can be prepared according to but not limited with the examples given below.

EXAMPLE 1

Preparation of Tris(Hydroxymethyl)Aminomethane Salt of Cefdinir 39.5 g of cefdinir (0.1 mol) and 18.7 g tris(hydroxymethyl) aminomethane (0.15 mol) is stirred in a mixture of 100 mL ethanol and 50 mL deionized water at a temperature of 25-35° C. The reaction mixture is then cooled to the room temperature and the formed precipitate is separated and recrystallized.

EXAMPLE 2

Preparation of 1-Deoxy-1-Methylamino-Sorbitol Salt of Cefdinir 39.5 g cefdinir (0.1 mol) and 58.6 g 1-Deoxy-1-methylamino-sorbitol (0.3 mol)is stirred in 100 mL of methanol at a temperature of 40° C. The reaction mixture is cooled in a cooler and the precipitate that forms is filtrated right away and purified by washing with cold methanol.

In all stages of the preparation of the molecules of invention; all the known polar, non-polar, protic and aprotic organic solvents and water, all the known purification methods such as extraction, recrystallization with solvent/anti-solvent, recrystallization with activated carbon, chromatographic techniques, distillation and filtration can be used.

In another aspect, molecules of invention can form during the manufacture or use of a pharmaceutical composition comprising cefdinir and an amine comprising more than one hydroxy group.

Solvent that can be used for the preparation and purification of the molecules of invention can be chosen from but not limited with a group comprising; water, ethanol, methanol, isopropanol, dimethylformamide, dimethylsulfoxide, methylenechloride, tetrahydrofuran, toluene, acetonitrile, hexane, heptane, diethylether, benzene, ethyl acetate, acetone, t-butyl alcohol, t-butyl methyl ether, chloroform, cyclohexane, 1,2-dichloroethane, 1,2-dimethoxyethane, dioxane, ethyl methyl ketone, ethylene glycol, 2-propanol, pyridine, triethylamine. Pharmaceutical compositions comprising cefdinir as an active agent Another aspect of the invention is related to water dispersible powders, tablet and granules comprising cefdinir as the active agent, formulations of these water dispersible powders, tablet, and granules comprising cefdinir as the active agent and process for preparation thereof. Surprisingly it was seen that when cefdinir, which is characterized with its low water solubility, is formulated with the water dispersible powder, tablet, as granule formulation disclosed in the present invention it disperses in water and forms homogenous cefdinir solution.

Accordingly, pharmaceutical dosage forms that are in the form of water dispersible powder, tablet or granule and suitable for use as a single dose;
a) will have a longer shelf life compared to the suspension forms since the dosage form in solid form is more stable and
b) has higher bioavailability and is easier to use for the patients compared to the solid dosage forms since it dissolves in water and disperses homogeneously prior to use.

Therefore water dispersible powder, tablet and granule formulation of the present invention has combined the advantages of the tablet and suspension forms and removes the disadvantages arising from these forms.

The term "water dispersible powder, tablet, and granule" comprises effervescent tablet, effervescent granules, effervescent powders, water dispersible tablets, water dispersible powders and water dispersible granules, water soluble tablets, water soluble powders, and water soluble granules.

Accordingly one aspect of the present invention is water dispersible powders, tablets, and granules comprising cefdinir as active agent.

Another aspect of the invention is water dispersible powder, tablet, and granule formulations comprising pharmaceutically acceptable excipients in addition to cefdinir which is used as an active agent.

Cefdinir has a hydrophobic character and for this reason it has wetting and low solubility problems. This leads to low bioavailability and problems related to development of water dispersible formulations.

Upon the investigations related to development of water dispersible powder, tablet and granule forms, the inventors has unexpectedly found that use of organic base in the formulation is effective for solving the water solubility problem of cefdinir.

Accordingly, in the present invention primary, secondary, tertiary amines and/or nitrogen containing heterocyclic compounds can be used as organic base.

Organic base that can be used in the formulation can be selected from a group comprising ethanolamine, isopropanolamine, 1-deoxy-1-methylamino-sorbitol, 1-deoxy-1-methylamino-D-glucitol, tris(hydroxymethyl)aminomethane, N-(tri(hydroxymethyl)methyl)glycine, N,N-Bis(2-hydroxyethyl)glycine, 2-methyl aminophenol. Preferably 1-deoxy-1-methylamino-sorbitol and tris(hydroxymethyl)aminomethane are used.

Cefdinir which can be used in the water dispersible powder, tablet, and granule formulations of the present invention can be present in the form of its solvates, hydrates, enetiomers, racemates, organic salts, inorganic salts, polymorphs, crystal, and amorphous forms or in free form and/or as a combination of these.

In the said formulation in addition to cefdinir and organic base, several other excipients such as binders, lubricants, humectants, disintegrants, basic agents, acidic agents, sweeteners, and optionally effervescent couples can be used.

In water dispersible powder, tablet and granule formulation of the invention, binder can be selected from, but not limited with, a group comprising ethyl cellulose, gelatine, hydroxy ethyl cellulose, hydroxy methyl cellulose, hydroxypropyl cellulose, hypromellose, magnesium aluminium silicate, methyl cellulose, povidone.

In water dispersible powder, tablet and granule formulation of the invention, lubricant can be selected from, but not limited with, a group comprising calcium stearate, magnesium stearate, polyethylene glycol, PEG6000, polyvinyl alcohol, potassium benzoate, sodium benzoate.

In water dispersible powder, tablet and granule formulation of the invention, humectant can be selected from, but not limited with, a group comprising anhydrous sodium sulphate, silica gel and potassium carbonate.

In water dispersible powder, tablet and granule formulation of the invention, disintegrant can be selected from, but not limited with, a group comprising carboxymethyl cellulose calcium, carboxymethyl cellulose sodium, microcrystalline cellulose, silicon dioxide, croscarmellose sodium, crospovidone, hydroxypropyl cellulose, methyl cellulose, povidone, magnesium aluminium silicate, starch, or a combination thereof.

In water dispersible powder, tablet and granule formulation of the invention, diluent can be selected from, but not limited with, a group comprising calcium carbonate, calcium sulfate, dibasic calcium phophate, tribasic calcium sulfate, calcium sulfate, microcrystalline cellulose, lactose, magnesium carbonate, magnesium oxide, maltodextrine, maltose, mannitol, sodium chloride, sorbitol, starch, xylitol, or a combination thereof.

In water dispersible powder, tablet and granule formulation of the invention, basic agent can be selected from, but not limited with, a group comprising potassium carbonate, potassium citrate, potassium hydroxide, sodium carbonate, sodium bicarbonate or combinations thereof. In water dispersible powder, tablet and granule formulation of the invention, acidic agent can be selected from, but not limited with, a group comprising acetic acid, citric acid, lactic acid, malic acid, phosphoric acid, propionic acid, tartaric acid, or combinations thereof.

In water dispersible powder, tablet and granule formulation of the invention, sweetener can be selected from, but not limited with, a group comprising acesulfame, aspartamate, dextrose, fructose, glucose, lactitol, maltitol, maltose, sorbitol, saccharide, sodium saccharide, sodium cyclamate, sucralose, sodium chloride, potassium chloride, sucrose, xylitol, or combinations thereof.

In water dispersible powder, tablet, and granule formulation of the invention, effervescent couple which is optionally used can be selected from, but not limited with, a group comprising citric acid, tartaric acid, malic acid, furmaric acid etc, as organic acid and sodium carbonate, sodium hydrogen carbonate, potassium carbonate, potassium hydrogen carbonate etc,. as organic base.

In water dispersible powder, tablet and granule formulation of the invention, 1-4000 mg of cefdinir or pharmaceutical salts, hydrates, solvates, or a combination thereof in an amount equivalent to that can be used.

In water dispersible powder, tablet and granule formulation of the invention; 5-60% of cefdinir or pharmaceutically acceptable solvates, hydrates, enantiomers, racemates, organic salts, inorganic salts, polymorphs, crystal/amorphous forms, 1-30% organic base, 1-30% binder, 0.1-3% lubricant, % 0.1-5% sweetener, 0.1-8% coloring and/or flavoring agent, and optionally 0-90% effervescent couple in an amount by total weight of the unit dose can be used.

In another aspect present invention relates to processes used for the preperation of water dispersible powder, tablet, and granule formulations comprising cefdinir as active agent and pharmaceutically acceptable excipients.

Accordingly, process used in present invention comprises granulation of cefdinir with conventional dry and/or wet granulation methods known in the art or mixing cefdinir and other excipients with a dry blending method and optionally pressing them in tablet form.

Water dispersible powder, tablet or granules according to the present invention can be prepared according to the examples given below. The examples are given for the sake of demonstrating the invention and the invention is not limited with these examples.

EXAMPLE 3

Formulation and Process for Preperation of Effervescent Granules

|  | % amount in unit dose | Amount in unit dose (mg) |
|---|---|---|
| Cefdinir | 30% | 600 mg |
| Organic base | 9% | 180 mg |
| Citric acid | 33% | 660 mg |
| Sodium hydrogen carbonate | 20% | 400 mg |
| Binder | 2.5% | 50 mg |
| Sweetener | 2.5% | 50 mg |
| Lubricant | 0.75% | 15 mg |
| Coloring agent | 1.25% | 25 mg |
| Flavouring agent | 1% | 20 mg |
| Total tablet weight | — | 2000 mg |

Formulation is obtained by granulation of sodium hydrogen carbonate and cefdinir with aqueous solution of organic base and then mixing the formed granules with citric acid and sweetener. The formed mixture is then granulated with a solution of binder. The granule obtained after this step is mixed with lubricant, coloring agent, sweetener and flavouring agent and optionally it can be compressed to obtain tablets.

EXAMPLE 4

Formulation and Process for Preparation of Water Dispersible Granules

|  | % amount in unit dose | Amount in unit dose (mg) |
|---|---|---|
| Cefdinir | %45 | 450 mg |
| Organic base | %21 | 210 mg |
| Binder | %23 | 230 mg |
| Sweetener | %4.5 | 45 mg |
| Lubricant | %2 | 20 mg |
| Coloring agent | %2 | 20 mg |
| Flavouring agent | %2.5 | 25 mg |
| Total tablet weight | — | 1000 mg |

Formulation can be obtained by granulation of cefdinir with aqueous solution of organic base and then mixing the formed granules with sweetener. The formed mixture is then granulated with a solution of binder. The granule obtained after this step is mixed with lubricant, coloring agent, sweetener and flavouring agent and optionally it can be compressed to obtain tablets.

In another aspect present invention relates to use of water dispersible powder, tablet and granule formulations comprising cefdinir and in addition to that pharmaceutically acceptable excipients for the treatment of infections caused by gram positive and gram negative bacteria.

Production Method for Effervescent Tablet

Another aspect of the invention is related to granulating cefdinir with an aqueous solution of organic base in a method for use in the preparation of effervescent formulation comprising cefdinir.

In another aspect, the present invention is related to the use of a production method comprising following the steps given below in the production of cefdinir formulations in the effervescent form. Therefore, said process comprises the following steps;

I. A granulation solution comprising water in an amount of 80-98% of the total water amount to be used in the process and organic basic agent is prepared, (first granulation solution)
II. Effervescent base and cefdinir are granulated with this granulation solution, (first granulation)
III. A granulation solution comprising water in an amount of 2-20% of the total water amount to be used in the process, ethanol and binding agent is prepared, (second granulation solution)
IV. The granules obtained in step III are mixed with effervescent acid and sweetener and granulated with the second granulation solution,
V. The granules obtained are dried and screened,
VI. Said granules are mixed with lubricant, flavoring agent, sweetener and coloring agent,
VII. The obtained composition is stored in accordance with the desired dosage form.

In the process in accordance with the invention, granulation of cefdinir with aqueous granulation solution comprising organic base prevents the agglomeration of this substance upon contact with water and this way dose uniformity of the final product was provided.

Accordingly, one aspect of the invention is the use of the process described above in the production of the effervescent compositions comprising cefdinir.

The effervescent formulation produced in accordance with the process of the present invention can be stored in tablet and/or sachet form.

Organic basic agent to be used in the present invention can be selected from primary, secondary, tertiary organic amines comprising at least one hydroxyl group (—OH) and/or heterocyclic compounds comprising nitrogen.

Organic base that can be used in the formulation can be selected from a group comprising ethanolamine, isopropanolamine, 1-deoxy-1-methylamino-sorbitol, 1-deoxy-1-methylamino-D-glucitol, tris(hydroxymethyl)aminomethane, N-(tri(hydroxymethyl)methyl)glycine, N,N-Bis(2-hydroxyethyl)glycine, 2-methyl aminophenol. Preferably 1-deoxy-1-methylamino-sorbitol and tris(hydroxymethyl)aminomethane are used.

Cefdinir which can be used in effervescent powder, tablet and granule formulations of the present invention can be present in the form of its solvates, hydrates, enetiomers, racemates, organic salts, inorganic salts, polymorphs, crystal and amorphous forms or in free form and/or as a combination of these.

Water, which is used as a granulation solution in the present invention, is in the deionized form.

Water amount to be used in first granulation solution is in the range of 80-98% of the water amount to be used in the process, preferably in the range of 85-96%. Water amount to be used in second granulation solution is in the range of 2-20% of the water amount to be used in the process, preferably in the range of 4-15%.

Binder, which can be used in the effervescent formulation that is produced by using the process in accordance with the present invention, can be selected from, but not limited to, a group comprising ethyl cellulose, gelatine, hydroxy ethyl cellulose, hydroxy methyl cellulose, hydroxypropyl cellulose, hypromellose, magnesium aluminium silicate, methyl cellulose, povidone. Preferably povidone is used.

Lubricant, which can be used in the effervescent formulation that is produced by using the process in accordance with the present invention, can be selected from, but not limited with, a group comprising calcium stearate, magnesium stearate, polyethylene glycol, PEG6000, polyvinyl alcohol, potassium benzoate, sodium benzoate.

Sweetener, which can be used in the effervescent formulation that is produced by using the process in accordance with the present invention, can be selected from, but not limited with, a group comprising acesulfame, aspartamate, dextrose, fructose, glucose, lactitol, maltitol, maltose, sorbitol, saccharide, sodium saccharide, sodium cyclamate, sucralose, sodium chloride, potassium chloride, sucrose, xylitol, or combinations thereof.

Sweetener, which can be used in the steps IV and VI of the described process, can be selected from the above group and also they can be same or different from each other.

Effervescent acid, which will used in the effervescent formulation that is produced by using the process in accordance with the present invention, can be selected from organic acids such as citric acid, tartaric acid, malic acid, fumaric acid and effervescent base can be selected from basic agents such as sodium carbonate, sodium hydrogen carbonate, potassium carbonate and potassium hydrogen carbonate.

In the effervescent formulation produced by the process in accordance with the present invention, 1-4000 mg of cefdinir or its pharmaceutically acceptable salts, hydrates, solvates, or a combination thereof in an amount equivalent to that can be used.

In the effervescent formulation produced by the process in accordance with the present invention, 5-60% of cefdinir or pharmaceutically acceptable solvates, hydrates, enantiomers, racemates, organic salts, inorganic salts, polymorphs, crystal/amorphous forms, 1-30% organic base, 1-30% binder, 0.1-3% lubricant, % 0.1-5% sweetener, and/or taste regulating agent, 0.1-8% coloring, and/or flavoring agent and 0.1-90% effervescent couple in an amount with respect to the total weight of the unit dose can be used.

In the cefdinir formulation produced by the process in accordance with the present invention, a second active agent can optionally be used. A second active agent can be selected from cefalosporins and beta-lactamase, preferably clavulanic acid or derivatives thereof is used.

In the cefdinir formulation produced by the process in accordance with the present invention, clavulanic acid, which can optionally be used, is used in the form of its solvates, hydrates, enantiomers, racemates, organic salts, inorganic salts, polymorphs, crystal/amorphous forms or free form or in a combination thereof. Preferably potassium clavulanate is used.

In the cefdinir formulation produced by the process in accordance with the present invention, optionally 50-500 mg of clavulanic acid or its pharmaceutically acceptable salts, hydrates, solvates or a combination thereof in an amount equivalent to that can be used.

Clavulanic acid and derivatives thereof (for example potassium clavulanate) are very sensitive to moisture. Therefore, in the pharmaceutical composition in accordance with the present invention, preferably potassium clavulanate is used together with a desiccant in a ratio of 1:1.

One or more than one of the following substances can be used as a desiccant; silica; colloidal silica, for instance colloidal silica anhydrous, Aerosil® 200, magnesium trisilicate, powdered cellulose, Cabosil®, magnesium oxide, calcium silicate, Syloid®, starch, microcrystalline cellulose, and talc.

In the cefdinir formulation produced by the process in accordance with the present invention, preferably potasium clavulanate is used together with syloid or microcrystalline cellulose in a ratio of 1:1.

In the cefdinir formulation produced by the process in accordance with the present invention, 5-90%, preferably 10-80% of clavulanic acid in an amount by total weight of the unit dose or pharmaceutically acceptable salts, hydrates, solvates or a combination thereof in an amount equivalent to that can be used.

Accordingly, in the cefdinir formulation produced by the process in accordance with the present invention, in cases where potasium clavulanate is used as the second active agent, said second active agent gets involved in the process in the steps II and/or IV and/or VI of the process.

In another aspect, potasium clavulanate can be granuled with cefdinir by using the granulation solution comprising organic base or it can be mixed with the granules comprising cefdinir and organic base and granuled by using the granulation solution comprising binder or it can be mixed with the granules including cefdinir dryly.

Effervescent formulations in accordance with the present invention can be prepared according to the following examples provided that they are not limited by these examples,

EXAMPLE 5

Formulation and Process for the Preparation of Effervescent Tablet

|  | % amount in unit dose |
|---|---|
| Cefdinir | 30% |
| Organic base | 9% |
| Citric acid | 33% |
| Sodium hydrogen carbonate | 20% |
| Binder | 2.5% |
| Sweetener | 2.5% |
| Lubricant | 0.75% |
| Coloring agent | 1.25% |
| Flavouring agent | 1% |

Formulation to be prepared in accordance with the present invention is obtained by granulation of sodium hydrogen carbonate and cefdinir with aqueous solution of organic base and then mixing the formed granules with citric acid and sweetener. The formed mixture is then granulated with a solution of binder. The granule obtained after this step is mixed with lubricant, coloring agent, sweetener and flavouring agent and preferably it is compressed in the form of tablets.

EXAMPLE 6

Formulation and Process for the Preparation of Effervescent Tablet

|  | % amount in unit dose |
|---|---|
| Cefdinir | 20% |
| Potassium clavulanate: syloid | 13% |
| Organic base | 9% |
| Citric acid | 30% |
| Sodium hydrogen carbonate | 20% |
| Binder | 2.5% |
| Sweetener | 2.5% |
| Lubricant | 0.75% |
| Coloring agent | 1.25% |
| Flavouring agent | 1% |

Formulation can be obtained by granulation of cefdinir with aqueous solution of organic base and then mixing the formed granules with sweetener, effervescent acid, and potassium clavulanate:syloid. The formed mixture is then granulated with a solution of binder. The granule obtained after this step is mixed with lubricant, coloring agent, sweetener, and flavoring agent and optionally it can be pressed as tablets.

In another aspect, present invention relates to use of effervescent formulations comprising cefdinir and in addition to that pharmaceutically acceptable excipients for the treatment of infections caused by gram positive and gram negative bacteria.

In another aspect pharmaceutical formulation prepared in accordance with the present invention, is used in the production of the drug to be used in the treatment and prophylaxis of upper respiratory tract infections such that ear, nose, throat, otitis media, sinusitis, tonsillitis, pharyngitis, lower respiratory tract infections such as pyelonephritis, cystitis and urethritis, skin and soft tissue infections such as froncle, pyoderma, impetigo and also gonorrhea and lyme diseases.

Effervescent tablet and granule formulation comprising cefixime

Another aspect of the invention is related to formulation of effervescent tablets and granules comprising cefixime and processes for preparation of these. Surprisingly it was found that effervescent tablets comprising cefixime, which has a low solubility, and formulated with the formulation given in the present invention dissolves in water and forms a homogenous cefixime solution.

Accordingly, the first aspect of the invention is effervescent tablet and granule formulations comprising cefixime.

The second aspect of the invention is use of cefixime in an amount 1-60%, preferably in an amount 5-50% and more preferably in an amount 10-40% in effervescent tablet and granule formulation of the present invention.

Cefixime used in the invention can be in monohydrate, dihydrate, trihydrate and/or anhydrous form.

Another aspect of the invention is pharmaceutical composition comprising cefixime and in addition to that pharmaceutically acceptable excipients.

Said pharmaceutical composition is formulated for effervescent tablet and granule forms. Accordingly, another aspect of the invention relates to pharmaceutical compositions for oral application, comprising cefixime and pharmaceutically acceptable excipients such as effervescent couple, sweetener, binder, water soluble lubricant and flavoring agents and other pharmaceutically acceptable excipients.

In tablet and granule composition of the present invention, cefixime can be present in an amount of 1-60%, effervescent couple can be present in an amount of 10-90%, sweetener can be present in an amount of 0.1-5%, binder can be present in an amount of 0.1-10%, water soluble lubricant can be present in an amount of 0.1-5%, flavoring agent can be present in an amount of 0.1-5%.

Said effervescent couple can be selected from organic acids such as citric acid, tartaric acid, malic acid, fumaric acid etc., basic agents such as sodium hydrogen carbonate, sodium carbonate, potassium carbonate, potassium hydrogen carbonate etc.

Sweetener that can be used in the tablet and granule formulations of the present invention can be selected from a group comprising acesulfame, aspartam, fructose, maltitol, xylitol, saccharine, sodium cyclamate, sucralose, sucrose. Preferably aspartame is used.

Water soluble lubricant that can be used in the tablet and granule formulations of the present invention can be selected from a group comprising PEG6000 and sodium benzoate.

In the tablet and granule formulations of the present invention 1-2000 mg of cefixime or its pharmaceutically acceptable salts, hydrates, solvates and/or a combination of these in an amount equivalent to 1-2000 mg cefixime can be used.

Binder that can be used in the tablet and granule formulations of the present invention can be selected from a group comprising; ethyl cellulose, gelatine, hypromellose, magnesium aluminium silicate, maltodextrin, polyethylene oxide and povidone. As a result of the experiments it was seen that the preferred binder is povidone. It was seen that in tablets in which cefixime:povidone ratio is 20:1, preferably 15:1 and most preferably 10:1 physical qualities such as friability and stability and chemical properties such as solubility and dispersibility have the desired characteristics and that the said ratio plays an important role in obtaining water soluble cefixime effervescent tablets and granules.

In general it is known that water soluble polymer based binders increase the disintegration time of the tablets however unlike what is expected it was seen that effervescent tablets formulated according to the formulation disclosed in the present invention disperses in a short time.

Accordingly, another aspect of the present invention is effervescent tablet formulations comprising cefixime and povidon in an amount such that cefixime:povidon ratio is 20:1, preferably 15:1 and more preferably 10:1.

Another aspect of the invention is use of the pharmaceutical compositions for the treatment of infections caused by gram positive and gram negative bacteria.

Another aspect of the invention is related to processes for use in the preparation of effervescent tablet and granules comprising cefixime. Said process comprises use of wet and/or dry granulation techniques present in the state of the art.

Although not limited with the following example, a process for the preparation of the effervescent tablet or granule according to the present invention comprises granulation of cefixime, effervescent couple, sweetener and binder with water or an aqueous solution, drying of the formed granules, mixing dried granules with flavoring agent and water soluble lubricant and optionally compressing the formed mixture in tablet pressing machine.

EXAMPLE 7

Formulation Examples for Effervescent Granules

| | % amount in unit dose | Amount in unit dose (mg) |
|---|---|---|
| Cefixime | 21.0% | 250 mg |
| Citric acid | 36.5% | 438 mg |
| Sodium hydrogen carbonate | 36.5% | 438 mg |

-continued

| | % amount in unit dose | Amount in unit dose (mg) |
|---|---|---|
| Binder | 2.1% | 25 mg |
| Sweetener | 2.1% | 25 mg |
| Lubricant | 0.5% | 6 mg |
| Flavouring agent | 1.3% | 16 mg |
| Total tablet weight | — | 1200 mg |

The invention claimed is:

1. A salt of Formula III

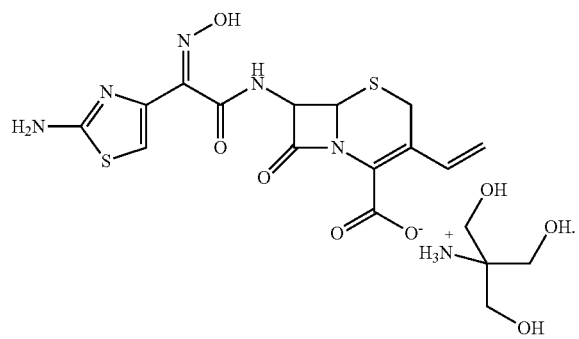

Formula III

2. A salt of Formula IV

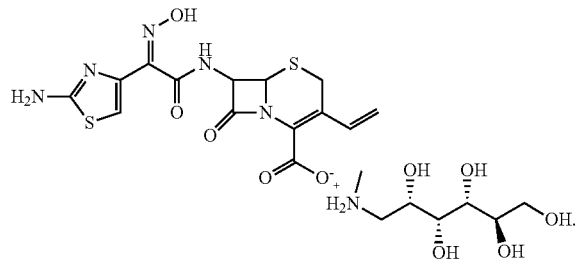

Formula IV

3. A process for preparing the salt according to claim 1, comprising the steps of:
   a) dissolving cefdinir and tris(hydroxymethyl)aminomethane in a suitable solvent and stirring at a temperature range of 0°-100°C.,
   b) separating the product that precipitates upon cooling of the reaction mixture, and purifying the product.

4. The process according to claim 3, wherein the solvent used in said process is selected from the group consisting of: water, ethanol, methanol, isopropanol, dimethylformamide, dimethylsulfoxide, methylenechloride, tetrahydrofuran, toluene, acetonitrile, hexane, heptanes, diethylether, benzene, ethyl acetate, acetone, t-butyl alcohol, t-butyl methyl ether, chloroform, cyclohexane, 1,2-dichloroethane, 1,2-dimethoxyethane, dioxane, methyl ethyl ketone, ethylene glycol, 2-propanol, pyridine, and triethylamine.

5. The process according to claim 3, wherein the reaction is carried out at a temperature of 10°-70°C.

6. The process according to claim 3, wherein the reaction is carried out at a temperature of 20°-60°C.

7. A process for preparing the salt according to claim 2, comprising the steps of:
   a) dissolving cefdinir and 1-deoxy-1-methylamino-sorbitol in a suitable solvent and stirring at a temperature range of 0°-100°C.,
   b) separating the product that precipitates upon cooling of the reaction mixture, and purifying the product.

8. The process according to claim 7, wherein the solvent used in said process is selected from the group consisting of: water, ethanol, methanol, isopropanol, dimethylformamide, dimethylsulfoxide, methylenechloride, tetrahydrofuran, toluene, acetonitrile, hexane, heptanes, diethylether, benzene, ethyl acetate, acetone, t-butyl alcohol, t-butyl methyl ether, chloroform, cyclohexane, 1,2-dichloroethane, 1,2-dimethoxyethane, dioxane, methyl ethyl ketone, ethylene glycol, 2-propanol, pyridine, and triethylamine.

9. The process according to claim 7, wherein the reaction is carried out at a temperature of 10°-70°C.

10. The process according to claim 7, wherein the reaction is carried out at a temperature of 20°-60°C.

* * * * *